United States Patent [19]

Perla et al.

[11] 4,020,154

[45] Apr. 26, 1977

[54] MANUFACTURE OF GAS-FREE DENTIFRICE

[75] Inventors: Giulio Perla; Giuseppe Mannara; Domenico Milesi, all of Rome, Italy

[73] Assignee: Colgate-Palmolive Company, New York, N.Y.

[22] Filed: Dec. 9, 1974

[21] Appl. No.: 531,254

Related U.S. Application Data

[63] Continuation of Ser. No. 325,804, Jan. 22, 1973, abandoned.

[52] U.S. Cl. .................................. 424/49; 424/52; 424/54; 424/55
[51] Int. Cl.² ........................................ A61K 7/16
[58] Field of Search ............................... 424/49, 52

[56] References Cited

UNITED STATES PATENTS 3,711,604  1/1973  Colondney ......................... 424/52

*Primary Examiner*—Lewis Gotts
*Assistant Examiner*—Cary Owens
*Attorney, Agent, or Firm*—Robert L. Stone; Murray M. Grill; Herbert S. Sylvester

[57] ABSTRACT

Gas-free paste or gel dentifrices are made by a process which includes producing a degassed gel of a gelling agent in a polyhydric alcohol, and admixing it with other dentifrice constituents, including powdered light weight polishing agent, under vacuum. Preferably, the powdered polishing agent is degassed in a vacuum hopper, before addition to the gel base in a mixer. Where no vacuum hopper or similar facilities are available, however, powdered polishing agent may be added to the gel in a suitable mixer with adequate head space and any gas present is removed from it by vacuum while it is resting on the surface of the gel, after which the polishing agent is mixed in with the gel.

13 Claims, 3 Drawing Figures

MANUFACTURE OF GAS-FREE DENTIFRICE

This is a continuation, of application Ser. No. 325,804, filed Jan. 22, 1973, and now abandoned.

This invention relates to degassing or deaeration of dentifrices, such as those which are in paste, cream or gel form and of thickness or viscosity great enough to entrap gas bubbles and hold them. More particularly, the invention is of a process of vacuum degassing light weight powdered constituents of the dentifrice, especially the polishing agent(s) but also including the gelling agent(s) and detergent(s) in the most effective processes, and admixing them and other dentifrice components under high vacuum. In another aspect of the invention, intended for use when powdered polishing agent can't be deaerated before addition to a mixer containing the gel, after the production of a gas-free gel the powdered polishing agent is admitted to a mixer containing the gel under vacuum and any entrained gas is removed by vacuum while the powder rests atop the gel, after which it is mixed in with the gel.

Dentifrices which are in paste or gel from are usually extrudable gelled products containing an insoluble finely divided polishing agent or mixture thereof which aids in the removal of deposits from the teeth and helps to polish and whiten them. Due to the thicknesses of the dentifrices and the manufacturing methods, which usually involve mixing or blending operations in which air or gases can become entrapped in the dentifrices, the products sometimes contain or air other gas bubbles, in very finely divided form. Even when such bubbles are not visible to the eye their presence can affect the density, flowability, stiffness, extrusion properties, stability and transparency or visual clarity of the dentifrices. Normally the presence of very small gas bubbles, usually air bubbles, in opaque toothpastes is not highly objectionable because in such products the bubbles are not usually seen by the human eye. However, when transparent or visually clear dentifrices are made it will usually be desirable to have them completely free of entrained gases because the larger bubbles are apparent to the consumer and the microscopic ones affect the visual clarity of the product, often causing it to appear cloudy. The microscopic bubbles, usually of diameters less than twenty microns, derive mostly from air occluded in the light weight polishing agent employed. Removal of gases from the dentifrices will often be desirable, even for opaque products, because gas-free dentifrices are more uniform, denser, and may be more stable.

Various methods have been disclosed for removing gases from viscous products. Application of vacuum to the final composition has been standard in the production of commercial dentifrices for many years. Solvents have been employed to diminish viscosities of dentifrices and intermediates so as to make gas bubble removal easier. Dentifrices have been deaerated by vacuum treatments applied to thin sections of films thereof. In some instances intermediate mixtures or ingredients have been deaerated. In a successfull process intermediate mixtures have been heated to promote the release of dissolved or entrained gases. Although in such cases, useful degassing has been effected, it has now been discovered that excellent visually clear dentifrices can be made by a simple, speedy and essentially trouble-free method which involves the deaeration of powdered constituents, especially the polishing agent, before production of the dentifrices. A similar result can be obtained by deaerating the polishing agent in the same vessel as the gel while it is resting atop the gel, before mixing together the polishing agent and the gel ingredients. However this last system is more difficult to operate and its use is often limited to installations not equipped with separate deaeration means for preliminarily deaerating the powdered polishing agent.

In accordance with the present invention a method for producing gas-free paste or gel dentifrices comprises making a gas-free polyhydric alcohol gel of a gelling agent, applying vacuum to it and admixing it under vacuum with degassed polishing agent(s) the optimum advantage being obtained when low bulk density powder is used. Especially preferred is the combination of such procedure with degassing of other powdered dentifrice components, e.g., gelling agent, detergent.

The invention will be readily understood from the following description of generic aspects, preferred embodiments and alternative forms thereof, taken in conjunction with the drawing in which.

Figure 1:
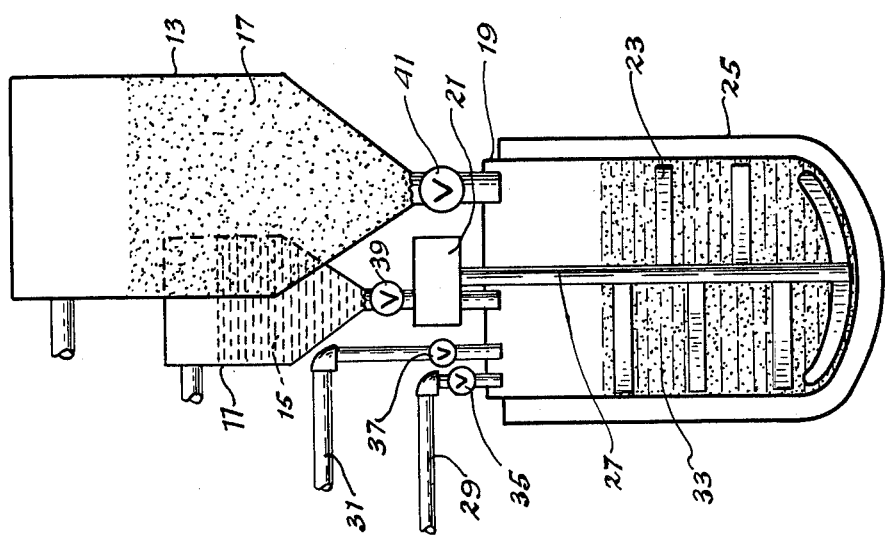
FIG. 1 is a partially sectioned, partially schematic vertical elevation of feeding and mixing apparatuses employed to make the dentifrice of this invention.

In FIG. 1 vacuum hoppers or vacuum feed tanks 11 and 13 are used to degas and supply gelling agent 15 and polishing agent 17, respectively, to a degassing, wall-wiping vacuum mixer 19. The mixer has a viarable speed motor or other drive 21 turning mixing and wiping blades 23 or includes stirring means of equivalent function, suitable for making pastes or gels under vacuum. It is equipped with a water or steam jacket 25 to assist in controlling the temperature of the contents of the mixer. In some cases, the blades 23 and shaft 27 may also be equipped with heat transfer means to speed the control of the contents temperature and make it more quickly responsive to the will of an operature. The mixer, which may be of the Dopp, Petzholdt, Unimix or other suitable type, is communicated with a source of vacuum by vacuum line 29. Liquid ingredients may be fed to the tank through line 31 from a source thereof, not shown.

As illustrated, mixer 19 contains a gelling agent polyhydric alcohol-water gel 33 which had been made by feeding polyhydric alcohol to the mixer, applying vacuum to the mixer adding gelling agent 15 to vacuum hopper 11, applying vacuum to the hopper to degas the gelling agent powder, adding the gelling agent under vacuum to the vacuum mixer, while mixing, subsequently adding more polyhydric alcohol to the mixer, still under vacuum, heating or not heating the mix while stirring depending on the gelling agent used, with the vacuum line and all other feed valves 35, 37, 39 and 41, respectively, closed, heating to about 60° C. and stirring fora period of about 30 minutes, to produce the gel. Subsequently, additional polyhydric alcohol(s), water and adjuvants, including dyes, are added through the liquid addition line and the product is cooled to about 30° C., after which the vacuum line is opened again. At this point, powdered polishing agent from vacuum hopper 13 is added to the mixer while the impeller is in motion and the mixer is under vacuum, and the degassed polishing agent is blended with the degassed gel. To facilitate flow of the polishing agent into the mixer from the vacuum hopper the pressure in the; mixer will be lower, e.g., about 5 to 50 mm. of mercury, preferably 10 to 25 mm. Hg lower, in the mixer. Subsequently other consituents of the dentifrice, such as synthetic organic detergent, thickening agents, flavors, sweeteners, etc., are added, with care being exercised to maintain the vacuum. Near the end of the operation chloroform or other solvent or flavor may be added to the dentifrice.

Figure 2:
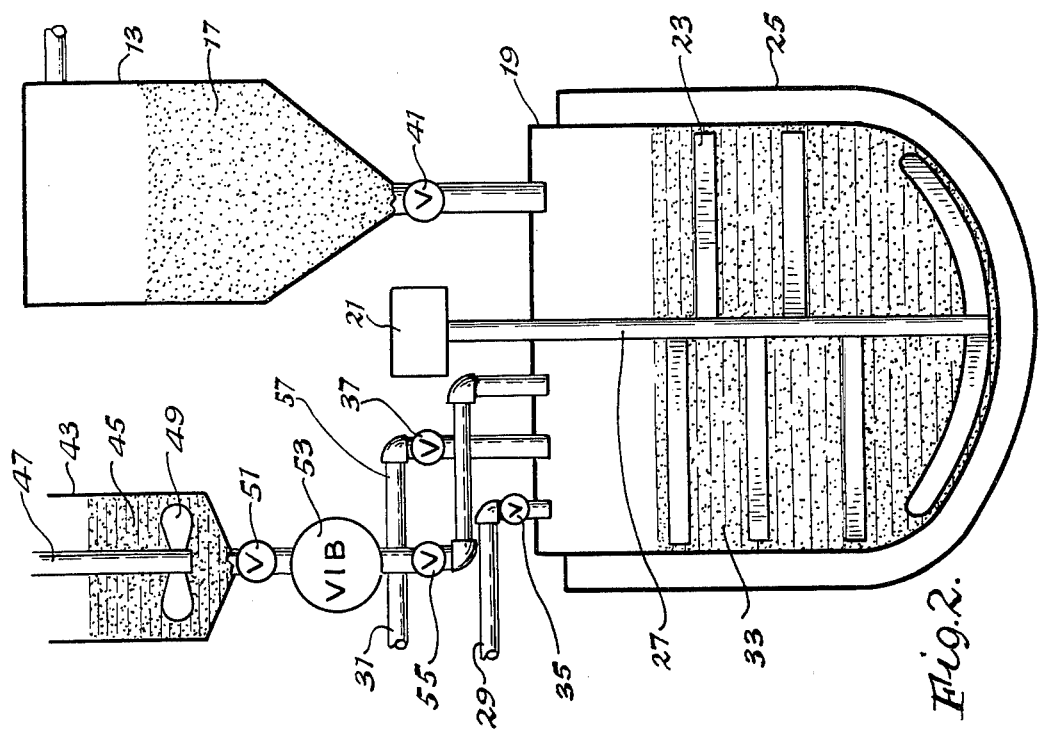
FIG. 2 is a view corresponding to FIG. 1 but with the gelling agent powder being mixed with polyol in a homogenizing mixer, e.g., a Vibroreactor, before being dropped to the mixer used for making the dentifrice.

In FIG. 2 the mixer, stirrer, vacuum hopper for polishing agent, vacuum line to the mixer, liquid inlet line and the associated valves are the same as in FIG. 1 but a different means is provided for producing a degassed gel to which the polishing agent is subsequently added. Mixing vessel 43 is normally open to the atmosphere although it could be also under vacuum and contains a preliminary mixture 45 of gelling agent powder and polyol medium which are stirred by a stirring means comprising sharft 47 and mixing blade 49. After a gross mixture of the gelling agent and polyhydric alcohol is made, valve 51 is opened and the mixture is fed to a Vibroreactor 53 or other suitable homogenizing device, which size-reduces lumps of gel and powder to particles or pieces in the size range of 0.02 to 1 mm. and facilitates their formation into a continuous and homogeneous gel. This is continuously dropped into a vessel 19 through valve 55 and line 57. The gel is thin enough to be easily degassed by the vacuum in vessel 19. After addition of the gel, polishing agent and other ingredients, all of which are added with the mixer operating and under vacuum, whenever possible, a degassed dentifrice is obtained. The Vibroreactor utilized is a high shear mixer or homogenizer equipped with a stator and a rotor having adjustable, close clearances and sharp edges on both the stator and the rotor to promote intimate mixing and reduction of any gel lumps. The charge to it can be at elevated temperature but it is preferably at about room temperature to save heating and cooling times. It may contain water or be essentially water-free. When a homogenizer if this type is not available, other procedures may be employed to produce deaerated gels, including deaeration of the gel powder in a vacuum hopper, (mentioned in the description of FIG. 1) and production of a thin gel with heating of the gel and standing being used to drive off any entrained gases.

Figure 3:
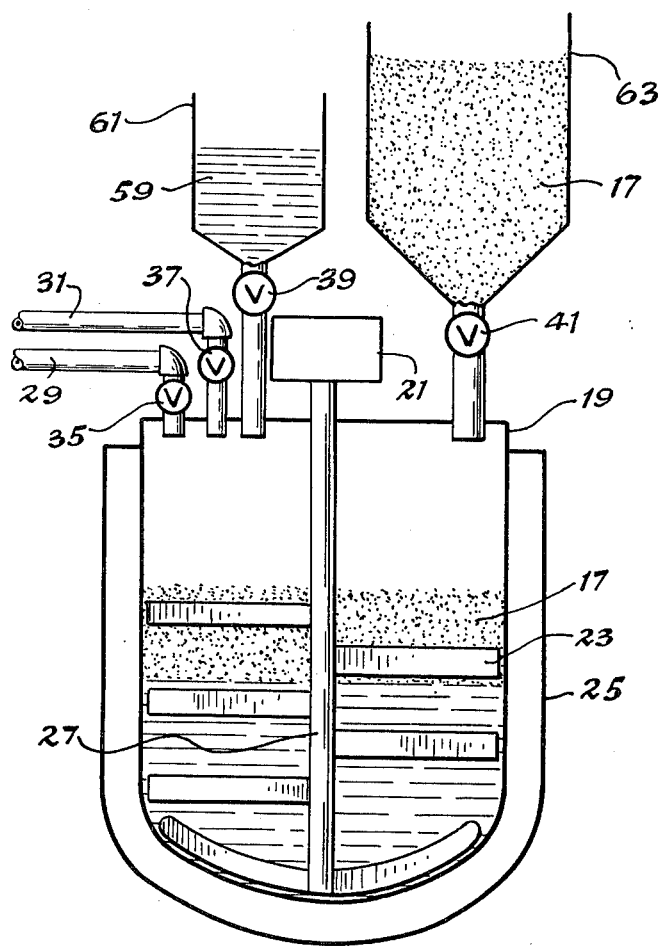
FIG. 3 is a view corresponding to FIG. 1 but with deaeration of the polishing agent being effected inside the dentifrice mixer.

In FIG. 3 an alternative method for making the present degassed dentifrices is shown wherein the structure is the same as that of FIG. 1 except for the absence of vacuum hoppers to charge the powders. In such a case, a comparatively thin gel 59 of gelling agent polyhydric alcohol in vessel 61 is made and is dropped to tank 19, with vacuum being applied to the tank to draw off the air from the gel. If desired, the gel may be heated to promote thinning and air removal. Then, finely divided light weight polishing agent 17 in open bin 63 is dropped onto the top of the gel while the mixer is not running. If desired, an absolute pressure of from 5 to 50 millimeters of mercury higher than that on the gel may be maintained as the polishing agent is dropped. Vacuum is applied to the mixer and the polishing agent in powdered form is seen to roil slightly, evidencing the release of gas from it. After the gas is released, mixing is begun and the polishing agent powder is blended in with the gel. Subsequent operations are similar to those described with respect to the dentifrice made in the apparatus of FIG. 1.

Dentifrice formulations of various types, including opaque and visually clear gelled products may be made in accordance with the methods of the present invention. Essentially all dentifrice gels and products which are extrudable from a squeeze tube will include gelling agent, polishing agent and vehicle. The vehicle will normally contain humectant(s) and water. Additionally, supplementary thickening agents, flavorings, colors and therapeutic ingredients may be present. In the opaque dentifrices based on insoluble inorganic polishing agents, these are generally present in large quantities and the amount of vehicle, including water, will usually be comparatively small, whereas when, as in clear dentifrices, lesser proportions of polishing materials are utilized there will be an increase in the proportions of vehicles and/or water. The amounts of flavoring materials, colorant and therapeutic constituents will generally be small, rarely exceeding 5% each and often being less than 2% each of the composition.

The gelling agents used to give body to the dentifrices of the present invention are known in the art and include the synthetic and natural gums and gum-like materials, such as silicated clays, sold under the trademarks Laponite CP and Laponite SP, alkali metal carboxymethyl celluloses, e.g., sodium carboxymethyl cellulose; hydroxyethyl carboxymethyl cellulose; hydroxypropyl ethyl cellulose; methyl cellulose; starched; starch glycolates; polyvinyl alcohol; polyvinyl pyrrolidone; hydrophilic colloidal carboxyvinyl polymers, such as those sold under the trademarks Carbopol 934 and Carbopol 940; diatomaceaous earth; bentorite and other natural clays (which may also function as polishing agents); proteinaceous materials, either animal-or vegetable-derived; Irish Moss; gum tragacanth; algenic acid derivatives, e.g., sodium alginate; carob bean gum and other such gums known to be useful for thickening dentifrices, which gums are listed in various cosmetic handbooks, including *Cosmetics: Science and Technology*, by Sagarin, 2nd printing, 1963, published by Interscience Publishers, Inc.

Of the gelling agent mentioned, those preferred include the Laponite CP and SP; carboxymethyl cellulose compounds; and Irish Moss. Of course, the various agents may be used in mixture or alone and preferred mixtures include those of a Laponite and sodium carboxymethyl cellulose.

Although they are not considered to be primary gelling agents, certain colloidal silicas such as Syloids 244 and 266 Aerosil, and pyrogenic silicas, sold as Cab-O-Sils, may be used for thickening or improving gelling properties. Generally, the gelling materials utilized are gellable with water or alcohols, especially with polyhydric alkanols of 3 to 6 hydroxyls and 3 to 6 carbon atoms per mole, e.g., sorbitol, glycerol. Preferably, the gel is formed with at least some water present with the gelling agent and the polyhydric alcohol.

The liquid vehicle of the dentifrice, together with the gelling agent(s) and other constituents, form an extrudable mass of a non-dripping consistency when extruded from a collapsible tube, such as one of aluminum, lead, or polyethylene. By the addition of more vehicle the dental cream can be thinner and conversely, by the addition of more solids or diminution of quantity of liquid present the product can be thickened, especially if more gelling agent is utilized. In most dentifrices the liquid portion thereof comprises sorbitol, glycerine and water, with the sorbitol usually being added as a commercially available aqueous solution. In replacement of part or in some cases, all of the sorbitol and glycerol, other suitable vehicles or humectants may also be employed. Thus, propylene glycol, polyethylene glycol, mannitol and polypropylene glycol may be used, normally with the molecular weights of such sompounds being from about 75to 500. Of course, to be employed in dentifrices such compounds must be physiologically acceptable and to make virtually clear dentifrices the final product, less polishing agent, should have a refractive index like that of the polishing agent.

The polishing agents utilized are usually very finely divided water insoluble powdered materials, preferably impalpable and of particle sizes such that they pass a 140 mesh screen of the U.S. Standard Sieve Series. Preferably, they are of 0.02 to 40 or 50 microns, most preferably from 1 to 20 microns in particle diameters, with the distribution of particle sizes being substantially normal over the ranges mentioned.

Among the polishing agents which are useful in the preparation of dentifrices may be mentioned sodium aluminosilicate; aluminum silicate, complex aluminosilicates; aluminum hydroxide (including alumina trihydrate); calcium aluminate; aluminum oxide; crystalline silica; colloidal silica; silica; xerogels; di- and tricalcium phosphates, hydrated and anhydrous dicalcium phosphates; insoluble sodium metaphosphates; magnesium phosphates; magnesium carbonate; calcium carbonate; calcium pyrophosphate; bentonite; talc; and calcium silicate. In the cases of many of these polishing agents the corresponding insoluble alkali metal or alkaline earth metal salts, e.g., the sodium salts, may be employed. The listing of polishing agents given here and other listings of constituents of the dentifrice composition in the specification are not considered to be exhaustive and therefore, for other materials of these types reference should be made to a standard handbook, such as *Cosmetics:Science and Technology*, ibid.

Most of the polishing agents mentioned are most useful in the preparation of opaque dentifrices but some of them such as the complex sodium aluminosilicates and the colloidal silicas, especially the silica xerogels, may be used for making clear dentifrices because their indexes of refraction approximate those of the balance of the dentifrice composition in an appropriate vehicle, such as sorbitol or sorbitolgycerol-water. The complex aluminosilicate salts mentioned above appear to contain interbonded silicas and alumina having Al-O-Si bonds, such as are described by Tamele in "Chemistry of the Surface and the Activity of Aluminum-Silica Cracking Catalysts", appearing in *Discussion of the Faraday Society*, No. 8, pages 270–279 (1950) and in a subsequent article in the same publication by Milliken et al., appearing at pages 279–90. Preferably, the polishing agents for use in the visually clear dentifrices contain up to about 20% of water, have a refractive index of 1.44 to 1.47 and a loose bulk density of about 0.07 to 0.12 g./ccm. and are of particle sizes in the 1 to 20 microns range. These complex aluminosilicate salts have been identified by various tradenames, including Degussa P820. Among appropriate xerogels for use in such formations is one marketed as Syloid 63. The light weight polishing agents, usually of a bulk density of 0.05 to 0.5, tend to be porous and to hold air or gas tightly. Degassing of them is more difficult after they are coated with liquid gel but can be readily effected when they are passed in a thin stream from a vacuum to a mixer under vacuum.

The synthetic organic detergents or surface active agents which may be used in the present compositions assist in emulsifying or otherwise despersing the components of the dentfrice uniformly and add their cleaning actions to the products. In some cases they are germicidal and assist in prophylaxis. The surface active material may be anionic, nonionic, ampholytic or cationic. It is generally preferred to employ as the major detersive constituent either an anionic or nonionic material or a mixture thereof. Of these, the anionics are considered to be superior. In addition to their surface active, emulsifying and detersive effects, such materials impart to the dentifrices desirable foaming properties. Generally, they will include lipophilic long chain fatty or poly-lower alkoxy groups, plus hydrophilic radicals. Usually, the anionic detergents will be in the forms of salts, especially water soluble salts of alkali or alkaline earth metals. Among those which are most useful may be mentioned the substantially saturated higher aliphatic acyl amides of lower aliphatic aminocarboxylic acid compounds, such as those having 12 to 16 carbon atoms in the fatty radicals, e.g., the sodium, potassium and ethanolamine salts of N-lauroyl sarcosine, N-myristoyl sarcosine and N-palmitoyl sarcosine. Such sarcosine compounds will normally be substantially free of soap or higher fatty acids so as to produce best anti-acid effects in the oral cavity. Other anionic detergents that are useful include the higher fatty acid monoglyceride monosulfates, such as the sodium salt of a monosulfate of monoglycerides of hydrogenated coconut oil fatty acids; higher alkyl sulfates, such as sodium lauryl sulfate; alkyl aryl sulfonates, such as linear dodecyl benzene sulfonates; olefin sulfonates; such as sodium higher olefin sulfonate in which the olefin group is of 12 to 22 carbon atoms; higher alkyl sulfoacetates; higher fatty acid esters of 1, 2-dihydroxypropane sulfonic acid; higher alkyl poly-lower alkoxy (10 to 100 alkoxies) sulfates; higher fatty acid soaps; and the like. In the specification the soluble soaps are considered to be synthetic organic detergents for the purpose of nomenclature. In the above description "higher" refers to chain lengths of 12 ro 22 carbon atoms, preferably 12 to 18 carbon atoms and most preferablt 12 to 16 carbon atoms. See the text *Surface Active Agents*, Vol. II (1958), by Schwartz, Perry and Berch for listings of other suitable detergents for the present compositions.

Instead of anionic detergents, nonionics can also be used, such as those which include chains of lower alkylene oxides, e.g., ethylene oxide, propylene oxide, in which there are present from 10 to 1000 or more moles of such lower alkylene oxides. Among such materials are the block copolymers of ethylene oxide. propylene oxide and propylene glycol, sold as Pluronics; the alkyl phenyl polyethoxy ethanols, sold as Igepals; the mixed copolymers of ethylene oxide, and propylene glycol sold as Ucons; and various other well known nonionics derived from higher fatty alcohols or acids and polyethylene oxides or glycols. The amphoteric agents and cationics, which may sometimes avoid the presence of cationics together with anionics, include quaternized imidazole derivatives, sold as "Miranols", such as Miranol $C_2M$, and cationic germicides such as di-isobutyl phenoxyethoxyethyl dimethyl benzyl ammonium chloride, benzyl dimethyl stearyl ammonium chloride and tertiary amines having a higher fatty alkyl group anf two polyoxyethylene groups attached to the nirogen thereof.

The water used in the product may be solvent with any portion of the composition, such as the solvent in the sorbitol solution or with the sodium N-lauroyl sarcoside detergent. It is is added to the composition, it will be preferrred to employ deionized water. Such water may be irradiated with ultraviolet light to assure sterility of the product, or the entire product may be so irradiated to decrease bacterial counts.

The flavoring materials employed, in addition to sweetening agents, are largely essential oils but may also include various flavoring aldehydes, esters, alcohols and simlar materials known in the art. Examples of the essential oils of spearmint, pepper mint, wintergreen, sassafras, clove sage, eucalpytus, marjoram, cinnammon, lemon, lime and orange. Also useful is the synthetic compound, methyl salicylate.

Solvent materials, which may be added near the end of the process may also possess flavoring properties but these are not considered to be flavors in the present description, except for chloroform. However, solvents such as ethanol, wthylene chloride and various halogenated aerosol propellant materials, such as Propellants 11, 12 114 and 122, may be used and can contribute some flavor or tang to the product.

A wide variety of adjuvant materials may also be present in these dentifrices but will not be recited at length here. For example, pH regulating materials or buffers; preservatives; fluorine-containing compounds, such as sodium fluoride, stannous fluoride and fluorphosphates, including sodium monofluorophosphate; antibacterial agents, coloring and whitening agents; pigments; silicones; chlorophyls; ammoniated compounds; fillers and soluble salts; decorative materials, e.g., finely ground mother-of-pearl; lubricants; and stabilizers may be present.

The advantages of the present invention are obtainable in the degassing of dentifrices of all types, in which powdered materials, such as light weight polishing agents, are employed. The present process is not limited in utility to the ingredients mentioned above, nor is it limited to particular formulations containing certain proportions of such materials. Yet, its advantages are considered to be most significant in those cases when the polishing agents are of the complex aluminisilicate, silica and other types useful to make clear gel dentifrices and in which the vehicles include sorbitol and/or glycerol. Using such materials, the extent of gas removal is significantly better than with comparable (in time) degassing techniques, as is evidenced in the case of clear dentifrices by an improved clarity of the product, allowing more efficient production and greater throughput for a production line on which the present process is employed. While it is not vital that particular proportions of constituents be utilized to obtain the advantages of this invention it has been found that within certain ranges those advantages are obtained to an economically significant extent.

The proportions of gelling agent in the present dentifrices will be sufficient to form an extrudable, shape retaining product which can be squeezed from a tube onto a toothbrush and will not fall between the bristles of the brush rather, will substantially maintain its shape thereon for at least 5 minutes. In almost all cases no more than 5% of gelling agent need be used and less than 0.1% will be of insufficient effect. In most instances from 0.1 to 3% will suffice, with a preferred range for the use of silicated clays, such as the Laponites, being from 1 to 4% and a preferred range for the use of sodium carboxymethyl cellulose thickeners being from 0.1 to 1.5%. When mixtures thereof are employed the preferred range may be from 0.2 to 2%. The proportion of additional thickeners, generally added at about the same time as the polishing agents, will normally be from 0 to 20% of the dentifrice, preferably from 2 to 8%, especially when Laponites or similar gelling agents are employed, and from 0 to 2% when carboxymethyl cellulose, Irish Moss or organic gums are used.

The liquid vehicle of the dentifrice, usually all or substantially all of polyhydric alcohol(s) will generally constitute from about 10 to 85% of the product, with 10 to 50% being a typical range for the production of opaque dentifrices and from 40 to 85% being most useful for the manufacture of visually clear products. Preferred ranges of vehicle contents in such products will be from 15 to 35% and 50 to 75%, respectively. The ratios of glycerol: sorbitol for the products will normally be from 1:3 to 10:1 and 1:5 to 5:1, respectively, with a most preferred range for the clear products being 1:3 to 1:1. In mentioning proportions of vehicles in the dentifrices the amounts of water present have been excluded. In opaque products, the water content will usually range from 5 to 35%, and will preferably be from 20 to 30%. The clear dentifrices will contain from 0 to 40% of water, preferably from 5 to 30%.

The polishing agent will be from 10 to 75% of the dentifrice, preferably being 20 to 75% for the opaque products and 10 to 50% for those which are visually clear.

The synthetic organic detergent content will usually be from 0.5 to 10%, preferably from 0.5 to 5% and most preferably from 1 to 3% thereof. If soaps are present as part of the synthetic detergent charges they will usually be limited to no more than 2% of the product. When nonionic detergents are employed they will normally be from 0.1 to 3%, preferably form 0.5 to 2% thereof and the proportions of amphoterics and cationics will be in the 0.1 to 1 to 2% area. Flavoring materials in the final product will usually be from 0.5 to 5%, preferably from 0.5 to 2.5% thereof. Such flavorings include both essential oils and sweetening agents which may be present (excluding sorbitol and glycerol). Of the sweetening materials, the synthetics, such as saccharin, will be present in a proportion from 0.05 to 0.3% but when natural sweetening agents, such as sugars, e.g., sucrose, lactose and glucose, are employed, this proportion may be increased and may be in the range of from 0.1 to 10%. The non-aqueous solvent in the product will usually be from 0 to 10% and preferably is from 0.1 to 5% thereof. Generally, such solventswill be volatile and will have boiling points at atmospheric pressure 80° C. or less, preferably from 50° to 70° C. The adjuvant content of the product will normally be held to a total of 5%, preferably less than 2%. For example, buffers such as tetrasodium pyrophosphate, will be held to from 0.1 to 0.5% and preservatives, such as sodium benzoate, will be at the 0.5 to 0.1 to 1% level.

In carrying out the process of this invention the powdered gelling agent and the powdered abrasive are degassed under vacuum before admixing with the vehicle, also under vacuum. Normally, following such procedures as are employed in the manufacture of dentifrices, the gelling agent powder will be blended in with the vehicle and/or water, and agitated In such actions, air or other gas (it may be desired to utilize a nitrogen or other gas blanket over the mixing materials) tends to be entrained in the powder and the vehicle and such entrainment is promoted by the thickening of the vehicle or aqueous system as gelling agent is dissolved or hydrated therein. Even when great care is taken in the mixing of gelling agent, polishing agent, detergent and vehicle there is some entrainment of gas. Following previous procedures, it would be attempted to remove such gas by vacuum treatment of the final product. Such a procedure is more time-consuming and less effective than that of the present invention.

In accordance with the present process, the gelling agent, in finely divided powder form, with particle sizes in the 5 to 2,000 microns range, preferably 10 to 100 microns, is weighed and fed to a hopper, tank or funnel in which it can be subjected to vacuum. The vacuum connection is made gradually by slowly opening an appropriate valve to a vacuum line, not specifically shown in the drawing, and with a sufficient head space above the level of the gelling agent in the vacuum container, e.g., 10 to 100 centimeters, the gas or air carried along with the powder may be "boiled" off. If a sight glass is used, it will be noted that the gas bubbles being removed from the powder cause activity at the surface of the powder somewhat resembling a boiling effect. Of course, the increase in the vacuum is gradual to keep the powder from being carried out the vacuum line.

In the most desirable embodiments of the invention the vacuum in the gel powder hopper or container is raised so that the absolute pressure is from 1 to 250 millimeters of mercury, preferably from 5 to 70 mm. Hg, after about 20 seconds to 10 minutes. In a similar manner, after weighing and addition of the polyhydric alcohol vehicle, preferably a 50 to 80% aqueous solution of sorbitol, most preferably a 70% solution of sorbitol, most preferably a 70% solution thereof, to the vacuum mixer, vacuum is drawn on it over about the same period of time and to substantially the same extent as for the gelling agent powder. It is preferred that the vacuum be exactly the same as that for the gel powder or lower, to the extent of a difference of 5 to 30 millimeters of mercury. Under such conditions, there will be no tendency of the gel powder to be stirred up in the hopper by the influx of gas from a mixer at higher pressure. Instead, its flow into the mixer will be aided. Of course, the design of the hopper should be such as to facilitate such flow and it has been found that of the conical or pyramidal walls of the hopper is less than about 70° preferably less than 65°, flow is encourages. Of course, the opening from the hopper should be sufficiently large to avoid bridging and in cases where the content of the mixer is from 500 to 5,000 liters, e.g., 1,200 liters, hopper valves and openings are preferably in the 15 to 25 cm. diameter range.

After the desired vacuums are reached in the gel powder hopper and the vacuum mixer, and after degassing of the gel powder is completed, the powder is added to the mixer by opening of the appropriate valves, while maintaining vacuum on the mixer. The mixer is operated at a comparatively low speed, often from 5 to 30 revolutions per minute. Then, maintaining the vacuum on the mixer, after the gel powder has been blended with the vehicle, additional polyhydric alcohol vehicle is added. Preferably, such additional vehicle will be glycerol and will be from 10 to 50% of the content of sorbitol in the mixer. The operations described will normally take place at about room temperature but they may be effected at temperatures in the range of 10° to 85° C. In some instances the glycerol may be blended with the sorbitol solution before addition of the gelling powder and in others a proportion of water in the product may be changed, either to be increased, or decreased, usually to within the 10 to 50% range.

After the slurry of gelling agent in vehicle(s) has been made it will be heated to a temperature sufficient to promote creation of the gel in a relatively short period of time, such as 10 minutes to 1 hour which temperature will usually be from 50° to 80° C. In some cases, the temperature can be raised to about 100° C. Of course, during such heating the vacuum lines will be shut off (otherwise vapor and steam would be discharged to them, interfering with their operations and changing the formulation of the product). After the end of the gelating step, which will often take about 10 minutes to 2 hours, generally about ½ hour, the product is cooled to a lower temperature, such as 10° to 45° C., preferably about 15° to 45° C and must preferably be slightly higher than room temperature, e.g., 30° C., and the mentioned vacuum is again applied to the gel. The gel described will usually contain about 0.3 to 4 parts of gelling agent, together with 13 to 40 parts of polyhydric alcohol and 5 to 15 parts of water. The polyhydric alcohol will preferably be 10 to 30 parts of sorbitol and 3 to 10 parts glycerol.

Instead of degassing the gelling agent powder in a vacuum hopper or equivalent container a mixture of gelling agent and humectant (sorbitol or glycerol mixture) may be made, homogenized and fed to a vacuum mixer or suitable other vessel for degassing, as was mentioned earlier in the description of FIG. 2. To be most successful this should be done with the gel being thin enough after homogenizing to be readily deaerated in the mixer. If this latter procedure is followed it may not be necessary to heat the gel during deaeration but heat may be used to speed the process.

Subsequent to making the gel the orders of additions of other dentifrice ingredients may be varied to obtain best processing advantages. In general, all of such ingredients and especially, the powdered polishing agent will be added under a vacuum such as that described previously. Generally, to thin the gel and make it more transparent, it is preferred that the next additives to the cooled gel should be liquid. For example, additional polyhydric alcohol(s), water and dilute aqueous or alcoholic solutions, such as color solutions, will usually be added next. These may be blended with the gelling agent. when the mix is sent through the Vibroreactor. In some embodiments of the invention, where the liquids are utilized, it may not be necessary to hold them under vacuum before addition but then they will usually be added below the surface of the gel do that no gas may be entrained with them. After addition of the liquid materials stirring is continued for from 20 seconds to 10 minutes so that a smooth product is made.

Then, the finely powdered polishing agent, such as aluminosilicates of particle sizes in the range of 0.02 to 100 microns, preferably from 0.002 to 40 to 50 microns and most preferably from 2 to 20 microns in particle diameters, is subjected to a vacuum of the type described above, preferably with the pressure being slightly higher, to the extent indicated, than the absolute pressure in the mixer, and with the mixer running, the polishing agent is added to it by the opening of the appropriate valve. Again the hopper design and sizing should be like those previously mentioned so as to promote ready flow of the polishing agent in the mixer. After all the polishing agent has been added, which may take from 30 seconds to 5 or 10 minutes, additions of other constituents may be made. In the absence of a vacuum hopper the light weight polishing agent and thickener may be deaerated in the mixer, as was previously mentioned in the description of FIG. 3. To avoid carry-over of any powder from the deposit on top of the gel surface, the gas space will be maintained at a height of from 10 to 100 centimeters and will usually be at least about twice the height of the layer of polishing agent on top of the gel. After removal of the gas from the polishing agent, mixing may be re-commenced, usually at a higher speed than previously employed, e.g., from 25 to 50 r.p.m.

After addition of the polishing agent by either of the described methods, a thickener, such as Syloid 244, may be added to one of the mentioned hoppers or an equivalent feeding device, where vacuum is applied to it and from which it is fed to the mixer under vacuum, again with the vacuum on the additive being less than that in the mixer. Such mixing may be effected in the same manner as was described for the polishing agent.

After the thickener has been distributed throughout the gel and polyhydric alcohol, a solution or suspension of detergent may be added, together with sweetening agents or other comparatively non-volatile flavors. In such a solution or suspension it is preferred that the ratio of detergent to polyhydric alcohol should be in the range of 1:1 to 1:10 preferably from 1:2 to 1:8. It is desirable to heat the polyhydric alcohol detergent-sweetener mix to a temperature in the 70° to 100° C. range or to an appropriate temperature to aid in deaerating the detergent before addition to the vacuum mixer. The solution or suspension is held at such temperature for a suitable period, usually from 5 minutes to one hour, before addition to the mixer. Such addition is effected by a method such as was previously described, either above the surface of the materials in the mixer with the mixer going, or below the surface of such materials, again with the mixer operating. Either after cooling to a lower temperature or at the elevated temperature mentioned the detergent mix is added to the Petzholdt or other suitable mixer without breaking the vacuum and mixing is continued for from 2 to 20 minutes. Instead of using a detergent solution or slurry, the dry deaerated detergent powder may be added in the same manner as was employed for the polishing agent addition. Then the vacuum valve is closed and chloroform or other flavors are added, after which mixing is continued for from 1 minute to 10 minutes. During this period, the vacuum may be diminished so that the absolute pressure is higher than before, due to the vapor tension of chloroform and/or flavors.

After termination of mixing, the vacuum is broken slowly, generally over a period of about 30 seconds to two minutes and the product may be discharged. Of course, care will be taken so that discharge is by a techique which does not entrain additional gas in the product.

The product made is a gas-free gel dentifrice which is excellent for cleaning the teeth, remains stable on storage and is attractive in appearance, containing no gas or air bubbles. It is gas-free in the sense that any gas contained is dissolved and so does not contribute to a cloudy appearance of a normally clear gel and does not adversely affect dentifrice properties. When clear dentifrices are made by this method they are sparkling clear and production times are cut significantly compared with other methods. Normally, over 95% of all gas present in the constituents of this composition is removed by this method and often the percentage is higher than 99%. The product contains so little undissolved gas as to be practically unmeasurable but it may be considered that such content is less than 0.1% by volume. The savings in processing times will usually be from 5 to 50% even when from 5 to 30% of the mixer volume is free head space (when polishing agent is deaerated in the mixer). The major improvement in efficiency is due to the prior removal of entrained gas from the gel base and from the polishing agent.

The following examples illustrate the invention. All parts are by weight and all temperature are in ° C, unless otherwise indicated.

EXAMPLE 1

|  | Parts |
|---|---|
| Sorbitol, 70%, aqueous solution | 44.6 |
| *Silicated clay (Laponite CP) | 2.0 |
| Glycerol, 98% pure | 25.0 |
| Dye, 5% aqueous solution | 0.2 |
| Deionized water | 3.0 |
| Complex sodium aluminosilicate, (Degussa P820) | 16.0 |
| Silica (Syloid No. 244) | 5.0 |
| Sodium N-lauroyl sarcosine | 2.0 |
| Saccharin | 0.2 |
| Flavoring (essential oils) | 1.0 |
| Flavoring (chloroform) | 1.0 |
| *[$Si_8Mg_{5.1}Li_{0.6}H_{7.6}O_{24}$]$^{0.6-}$-Na$^{+0.6}$. | |

Employing a jacketed Petzholdt vacuum mixer of the scraping blade type, equipped with polytetrafluoroethylene coated blades and heat transfer means in the jacket and of a capacity of 1,200 liters, 1200 kilograms of a clear gel dentifrice are made. 37.3 Percent of the batch weight of a 70% solids aqueous sorbitol solution is weighed out and pumped to a tank from which it is transferred to the Petzholdt mixer or another similar wiping blade mixer of the type previously described in the specification, filling about 1/4 of the mixer. The vacuum line is opened and a vacuum of 730 mm. Hg (30 mm. Hg absolute pressure) is obtained in the mixer and held for about two minutes, after which the mixer and the sorbitol solution are considered to be deaerated. The 2% of the formula weight of the Laponite CP gelling agent is weighed out and delivered to a vacuum hopper, wherein the pressure is diminished to 30 mm. Hg, where it is held for about 5 mintes. Removal of gas from the powder is evidenced by agitation of the upper powder surface. The silicated clay powder is then fed to the mixer by gradual opening of the 80 mm. delivery valve and with the mixer operating at 20 r.p.m., while maintaining the vacuum, blending is continued for eight minutes (from 2 to 20 minutes are usually employed) until the Laponite is dispersed and any small amount of residual gas has been removed. Then, a portion of the glycerol amounting to 5.1% of the final dentifrice charge is added, without breaking the vacuum, and the total mix is raised to a temperature of 60° C., the vacuum lines are closed and heating is continued at this temperature for an additional 30 minutes to produce the gel. Next, there is added to the gelled mix 7.4% of 70% sorbitol solution, 11.9% of glycerol (98%), 0.2% of color solution and 3.0% of deionized water, all being calculated on the finished product basis. After this thinning of the gel with the additional polyhydric alcohols and water, and subsequent cooling to 30° C., with stirring, the complex aluminosilicate polishing agent is fed to the vacuum hopper and the vacuum therein is brought to an absolute pressure of about 40 mm. Hg, which is about 10 mm. Hg less vacuum than that in the mixer. The vacuum is so applied for about 4 minutes, after which the polishing agent is fed to the mixer with the mixer turning at 25 r.p.m. The vacuum is maintained and mixing continues for five to fifteen minutes, after which similarly deaerated Syloid 244 is added and blended into the gel by mixing for an additional 5 minutes at about 50 r.p.m. In modifications of the process the polishing agent is blended with the gel over periods of 20 seconds to 1 hour, preferably 20 seconds to 20 minutes and more preferably 5 to 20 minutes. After the polishing agent and thickener are blended with the rest of the gel ingredients, there are added 8.0 parts of glycerol, 2.0 parts of sodium N-lauroyl sarcoside and 0.2 part of saccharine, all of which are first pre-mixed and heated to 90° C. to aid in deaeration of the detergent solution. Such deaerating heating at 90° C. lasts for about five minutes and after completion thereof the solution is added to the mixer without breaking vacuum and mixing is continued for about 8 minutes.

Next, the vacuum line is closed and the essential oil flavor is added, followed by mixing for 3 minutes without a break in the vacuum and then chloroform is added and mixing is continued for 5 minutes. Vacuum is maintained below 210 mm. Hg during such mixing. Mixing is then halted, the vacuum is broken gradually over a period of about 1 minute and the dentifrice is ready for discharge. The dentifrice produced is then transferred to a filling machine, with special care being taken to avoid any air entrainment, and it is filled into tubes, which are then crimped, packed, cased and sent to storage for shipment to warehouses and retail outlets.

The dentifrice made is an excellent cleaner for the teeth and maintains its clear appearance over normal storage periods. When compared with dentifrices of similar or identical formulations made by conventional deaeration methods (the final mix is deaerated without preliminary attempts to remove air or other gases from the ingredients or intermediate mixes), the differences in clarity are apparent to all viewers, with the "experimental" products being superior. Also if the processing times for both methods are held the same such differences are even more obvious.

When the above formula for the manufacture of a clear gel dentifrice is modified so that the complex sodium aluminosilicate is replaced by silica xerogel, such as Syloid 63, an excellent gas-free product is also made. Similarly, when in either of such clear gel formulations the gelling agent is replaced by sodium carboxymethyl cellulose (0.4% of the quantity) or by a mixture of 1% of Laponite CP or SP and 0.2% of sodium carboxymethyl cellulose, a useful clear dentifrice is also made, free of entrained gas. However, the formulations containing Laponite appear to be more stable on storage than those based on Sodium CMC. Replacement of the sarcosine detergent with sodium lauryl sulfate also produces a satisfactory experimental dentifrice. When the ratios of polishing agent, thickener, detergent and flavor are varied within the 10 to 50; 0 to 20; 1 to 5; and 0.1 to 5 range (parts by weight) excellent products are also obtainable.

Modifications in the manufacturing procedure described above are made and gas-free dentifrices are still produced. Thus, if chloroform is omitted entirely from the product it will still be gas-free. When the only preliminary degassing steps are those practiced on the gelling agent and and the polishing agent, with which it is blended, improved results are noted, compared to products made without such procedures being followed, even if subsequent materials are added without special care being taken to degas them. However, in such cases efforts should be made to minimize gas entrainment in the various other materials and to utilize mixing of such a type that it does not develope rapidly moving vortexes in the mixing dentifrices. When the vacuum conditions mentioned are altered within the ranges given, degassification is effected too, with the most satisfactory results being obtained when the vacuums employed are greater, within the ranges given. When the particle sizes of the powdered materials are changed within the ranges given, best results are obtained, insofar as degassing is concerned, when larger particles within the ranges are employed. However, as in the above experiments the ranges utilized within the middle parts of ranges given in the specification because of the desirability of rapid dissolving or dispersion, and in the case of the polishing agent, the need to have it small enough so that scratching of teeth is minimal and polishing is satisfactory, which often requires that the powder be substantially impalable. For example, the gelling agent powder is from 10 to 100 microns in particle diameters and the polishing agent is from 1 to 20 microns in size.

When minor proportions of adjuvants are also employed within the ranges described in the specification, such as bactericides, preservatives, antioxidants, buffering agents and coloring materials or pigments, the degassing is not adversely affected by their presences.

EXAMPLE 2

| | Parts |
|---|---|
| Glycerol | 26.0 |
| Sodium carboxymethyl cellulose | 0.8 |
| Saccharin | 0.1 |
| Sorbitol, (70% solids, aqueous solution) | 45.9 |
| Deionized water | 3.0 |
| Color solution (95% water) | 0.2 |
| Sodium N-lauroyl sarcosine | 2.0 |
| Sodium aluminosilicate (Degussa P-820) | 21.0 |
| Flavor | 1.0 |

A clear dentifrice of the above formula is made by weighing the glycerol into a tank and discharging it from the tank to a Petzholdt vacuum mixer of the high shear, close tolerance, rotor-stator type described in Example 1. Vacuum is applied to the mixer so that the absolute pressure is reduced to 28 mm Hg. Meanwhile the sodium carboxymethyl cellulose and saccharin are blended together in a vacuum hopper and the vacuum is applied to this mixture to the same extent as in the Petzholdt mixer. Vacuum is maintained on the powders for a period of three minutes, during which they are degassed and then, with the mixer operating at a low speed, about 20 r.p.m., the deaerated powders are added to the mixer from the vacuum hopper taking care to maintain the vacuum in the mixer. The vacuum is broken in the hopper after completion of the addition of the powders. Next, the sorbitol, water and color solution are blended together and are added to the mixer, with operation being at a higher speed, about 40 r.p.m., again avoiding breaking of any vacuum in the mixer. Subsequent to the addition, which takes three minutes, mixing is continued for another 10 minutes. Then, all the polishing agent and the sodium N-lauroyl sarcoside, previously blended together in the hopper, are deaerated at an absolute pressure of about 50 mm. Hg, which takes about two minutes, after which they are fed to the mixer while it is operating at about 70 r.p.m. Mixing is continued for about 20 minutes, after which flavor is added and an additional 10 minutes of mixing is employed to blend the flavor satisfactorily with the other constiuents.

The product obtained is then ready for filling into dentifrice tubes. It is an effective sparkling clear "transparent" dentifrice.

When changes are made in the formulation, wherein thickening materials such as silica aerogels, e.g., Cab-O-Sil M-5, are added in minor quantities, e.g., 2–4%, a good deaerated product is obtained. Also, when sodium lauryl sulfate is substituted for the sodium N-lauroyl sarcosine, no significant difference in the clear dentifrice is noted, except that the thickness of the dentifrice appears to be more responsive to electrolyte content in the presence of the sulfate detergent. Similar formulation changes or processing changes within the scope of the specification also produce good degassed, effective, stable dentifrices.

The process of Example 2 is repeated with conventional dentifrice formulations of the opaque type, based on dicalcium phosphate in place of the complex sodium aluminosilicate and on sodium carboxymethyl cellulose instead of the silicated clay gelling agent. Proportions of the other materials are maintained the same. By following the technique described above, improved degassing is obtained, compared to the conventional methods, in a shorter period of time. Thus, when the "experimental" opaque dentifrices of the described formula are tested for the presence of undissolved gas by the microscope slide test (a specimen of dentifrice is pressed between glass slides and visually observed for the presence of bubbles), no entrained air is found but in those products which are deaerated only by the application of vacuum after mixing of ingredients, even when longer vacuum application times are employed, the air bubbles are visible.

EXAMPLE 3

The procedure of Example 1 is followed except for the use of a Vibroreactor homogenizer to produce an initial gel, which is fed to the Petzholdt mixer, as illustrated in FIG. 2, without the need for preliminary vacuum treatment of the gelling agent powder to remove occluded gases. Following this procedure 37.3 parts of a 70% aqueous sorbitol solution, 5.1 parts of 98% pure glycerine and 1.5 parts of Laponite CP (or SP) are first mixed together and then fed to a Vibroreactor to produce an excellent gel of particle sizes, after passing through the Vibroreactor, in the range of 0.03 to 0.5 mm. diameter. This homogenized product is fed to the Petzholdt mixer to form a gel heel therein at about 30 mm. Hg absolute pressure and a temperature of about 25° C. The gel is thin enough as it emerges from the homogenizer to be readily deaerated as it flows into the mixer. After addition of the gel, the procedure of Example 1 is followed.

The major advantage of utilizing this method for the manufacture of gel dentifrices is in the rapid mixing and deaeration which may be effected, without the need for a lengthier residence time for the powdered gel in a vacuum hopper before feeding to the mixer. The method is particularly useful for degassing of the silicated clays, which tend to be more difficult to produce in a gas-free state than are the organic gums such as sodium CMC.

EXAMPLE 4

Instead of following the procedure of Example 1, with respect to preparing the gel in the mixer under vacuum, it is prepared by mixer the 25 parts of glycerol, and 44.6 parts of 70% solids sorbitol and admixing with it 2.0 parts of Laponite CP. The gel is mixed for about an hour and allowed to stand for ten hours, after which it is again mixed and it is found at that time that the gel is smooth and essentially gas-free. It may be heated to 50° C. and held for an addtional hour or more to further aid in degassing but this is not necessary. The gel is then added to the mixer of Example 1 and the other ingredients are blended in with it following the procedure described in Example 2. In some cases, the sodium N-lauroyl sarcosin is blended with half of the glycerol and water taken from thr gel ingredients and then is deaerated by being heated to an elevated temperature, 70° C., and held there for about one hour. In either case the degassed gel is charged to the mixer and the manufacturing procedure is otherwise the same as in Example 2. The products made are essentially the same as those previously described in Example 2.

EXAMPLE 5

The procedure of Example 3 is followed except that a vacuum hopper is not employed for deaerating the polishing agent before addition to the gel in the mixer. Instead, the polishing agent is dropped onto the surface of a gel in the mixer, on which it forms a layer about half as thick as the head space above it, and a pressure of 30 mm. Hg is held in the mixer for ten minutes, during which time the polishing agent is degassed. Then, the mixer is started and is operated at about 40 r.p.m. for about 20 minutes to blend the polishing agent with the gel, after which the procedure followed is that of Example 3. The use of the in-mixer deaeration technique will normally be limited to those cases when vacuum hopper is available because of the difficulty of satisfactorily blending the powder and completely deaerating all of it in the mixer by this method. However, the product obtained is almost as good as those obtained following the procedures of Examples 1 and 3. In some cases, the thickening agent or agents may also be blended with the polishing agent and deaerated in the same manner or subsequent to deaeration of the polishing agent.

The invention has been described with respect to illustrations and examples thereof but is not to be considered to be limited to these, since it is evident that equivalents be substituted for the materials or procedures recited without departing from the spirit of the invention or the ambit of the discovery disclosed herein.

What is claimed is:

1. In a method for the manufacture of a dentifrice by mixing a gel of a gelling agent and a polyhydric alcohol with a powdered polishing agent which is at least ten percent of the dentifrice, an improvement for obtaining the dentifrice in gas-free form which comprises preparing the gel in gas-free form, applying vacuum to the gel and admixing it under vacuum with degassed powdered polishing agent.

2. A method according to claim 1 wherein said powdered polishing agent is of a low bulk density, of 0.05 to 0.5 gram per cubic centimeter.

3. A method according to claim 2 wherein the dentifrice is a visually clear gel containing a polishing agent of about the same refractive index as the rest of the gel, the gelling agent is selected from the group consisting of organic and inorganic gums, the polyhydric alcohol is selected from the group consisting of aqueous solutions of sorbitol and glycerol and of mixtures thereof, the polishing agent is selected from the group consisting of complex aluminosilicates and silica gels, the vacuums employed are such that the corresponding absolute pressures are from about 1 to 250 millimeters of mercury and the temperature of admixture is in the range of about 10° to 85° C.

4. A method according to claim 3 wherein the degassing of the gel is effected by degassing a powdered gelling agent which is selected from the group consisting of silicated clay, sodium carboxymethyl cellulose and Irish Moss of particle sizes in the range of about 5 to 2,000 microns, the polyhydric alcohol is an aqueous solution of sorbitol at a concentration of from about 50 to 80%, the polishing agent is selected from the group consisting of sodium aluminosilicate and silica xerogel, of a bulk density of 0.05 to 0.5 gram per liter, the polishing agent is degassed under vacuum before mixing with the gel, the vacuums employed are such that the absolute pressures are from about 5 to 70 millimeters of mercury, the temperatures of degassing and admixture are in the range of about 10° to 40° C. and the times for effecting degassing are from about 20 seconds to 20 minutes each.

5. A method according to claim 4 wherein the degassing operations are effected in a vacuum mixer, the degassed gelling agent is added to polyhydric alcohol under vacuum with mixing, additional polyhydric alcohol is added to the degassed mixture of gelling agent and polyhydric alcohol while maintaining the vacuum and the resulting mixture is heated to a temperature of about 50° to 80° C. for a period of from 10 minutes to one hour in the closed mixer to produce a gel.

6. A method according to claim 4 wherein after the production of the gelling agent-polyhydric alcohol gel, additional amounts of dentifrice constituents, in liquid form, including sorbitol, glycerol and water, are admixed therewith, under vacuum.

7. A method according to claim 4 wherein the mixture of gelling agent and polyhydric alcohol(s) includes from 10 to 50 parts of sorbitol, from 0.2 to 4 parts of gelling agent selected from the group consisting of synthetic silicated clay and sodium carboxymethyl cellulose and from 3 to 10 parts of glycerol.

8. A method according to claim 6 wherein, after production of a gel of polyhydric alcohol and gelling agent, there is admixed with such gel at a temperature in the range of about 15° to 45° C., under vacuum, degassed polishing agent, degassed thickener, degassed polyhydric alcohol-detergent liquid and flavor.

9. A method according to claim 3 wherein the polishing agent is added to the gel and is rested atop the gel in the free space in the mixer above the top of the gel, which free space, excluding the height occupied by the polishing agent when added, is at least twice as high as the height of the polishing agent above the top of the gel, and vacuum is applied to the mixer to remove entrained gas from the polishing agent.

10. A method for the manufacture of gas-free dentifrice which comprises making a gas-free gel of a gum gelling agent and a polyhydric alkanol of 3 to 6 carbon atoms and from 3 to 6 hydroxyl groups, applying vacuum to such gel and admixing it under vacuum with a degassed powdered polishing agent, the amount of such gum gelling agent, alkanol and polishing agent being such as to provide a dentifrice containing 0.1 to 5 weight percent of gelling agent, 10 to 85 weight percent of polyhydric alkanol and 10 to 75 weight percent of polishing agent.

11. A method according to claim 8 wherein there is present in the final dentifrice from 10 to 50 parts of polishing agent having particle sizes in the 0.02 to 50 micron range, 2 to 10 parts of synthetic inorganic thickener, 1 to 5 parts of synthetic organic detergent and 0.1 to 5 parts of flavor.

12. A method according to claim 11 in which the polishing agent is sodium aluminosilicate, the thickener is a colloidal silica, and the detergent is sodium N-lauroyl sarcosine.

13. A method according to claim 3 wherein all powdered ingredients of the dentifrice are degassed before blending with other ingredients and all such blendings are effected under vacuums.

* * * * *